US012496435B2

(12) United States Patent
Ding

(10) Patent No.: US 12,496,435 B2
(45) Date of Patent: Dec. 16, 2025

(54) BALLOON DEVICE AND A MEDICAL DEVICE COMPRISING IT

(71) Applicant: Qiwei medical technology (Shenzhen) Co., Ltd, Guangdong (CN)

(72) Inventor: Haiyan Ding, Beijing (CN)

(73) Assignee: QIWEI MEDICAL TECHNOLOGY (SHENZHEN) CO., LTD, Guangdong (CN)

(*) Notice: Subject to any disclaimer, the term of this patent is extended or adjusted under 35 U.S.C. 154(b) by 831 days.

(21) Appl. No.: 17/774,029

(22) PCT Filed: Aug. 10, 2020

(86) PCT No.: PCT/CN2020/108088
§ 371 (c)(1),
(2) Date: May 3, 2022

(87) PCT Pub. No.: WO2021/103650
PCT Pub. Date: Jun. 3, 2021

(65) Prior Publication Data

US 2022/0323725 A1 Oct. 13, 2022

(30) Foreign Application Priority Data

Nov. 25, 2019 (CN) ......................... 201911164659.X
Jun. 10, 2020 (CN) ......................... 202010525747.4

(51) Int. Cl.
*A61M 25/10* (2013.01)
*A61L 29/16* (2006.01)

(52) U.S. Cl.
CPC ............ *A61M 25/10* (2013.01); *A61L 29/16* (2013.01)

(58) Field of Classification Search
CPC ........... A61M 25/1002; A61M 25/104; A61M 2025/1047; A61M 2025/105;
(Continued)

(56) References Cited

U.S. PATENT DOCUMENTS

2002/0177866 A1* 11/2002 Weikel .............. A61B 17/7258 606/192
2007/0032787 A1 2/2007 Hassett et al.
(Continued)

FOREIGN PATENT DOCUMENTS

CN 102512747 A 6/2012
CN 103635226 A 3/2014
(Continued)

OTHER PUBLICATIONS

International Search Report dated Nov. 13, 2020 issued in PCT/CN2020/108088.
(Continued)

*Primary Examiner* — Kami A Bosworth
(74) *Attorney, Agent, or Firm* — Scully, Scott, Murphy & Presser, P.C.

(57) ABSTRACT

This application disclosed a balloon device, comprising: a balloon catheter, and a balloon arranged on the balloon catheter, the balloon has a front end portion and a rear end portion in a longitudinal direction, and a pharmaceutical composition is provided on an outer surface of at least one of the front end portion and the rear end portion. The end drug coated balloon disclosed in this application combined with the existing instruments to treat the fistula can realize the continuous opening of the atrial septal fistula, prevent the atrial septal fistula from closing naturally in a short time, and achieve the effect of reducing cardiac preload and treating heart failure in a long time.

10 Claims, 11 Drawing Sheets

(58) Field of Classification Search
CPC .. A61M 2025/1052; A61M 2025/1043; A61M 2025/1054; A61M 2210/125; A61M 2210/127; A61B 17/12136; A61B 17/12122; A61B 2017/00575; A61B 2017/00592; A61B 2017/00597; A61B 2017/00641
See application file for complete search history.

(56) References Cited

U.S. PATENT DOCUMENTS

| | | | | |
|---|---|---|---|---|
| 2007/0185444 | A1* | 8/2007 | Euteneuer | A61M 25/1002 604/96.01 |
| 2008/0215008 | A1 | 9/2008 | Nance et al. | |
| 2009/0076447 | A1* | 3/2009 | Casas | A61M 25/04 604/96.01 |
| 2011/0230821 | A1 | 9/2011 | Babic | |
| 2014/0276530 | A1 | 9/2014 | Gianotti | |
| 2015/0238736 | A1* | 8/2015 | Zeng | A61M 25/1002 604/103.02 |
| 2015/0297872 | A1 | 10/2015 | Carpenter et al. | |
| 2015/0352341 | A1* | 12/2015 | Chandler | A61M 25/0068 604/97.02 |
| 2017/0157369 | A1* | 6/2017 | Faith | A61M 25/10181 |
| 2019/0015639 | A1 | 1/2019 | Wang et al. | |
| 2019/0117242 | A1* | 4/2019 | Lawinger | A61B 18/26 |

FOREIGN PATENT DOCUMENTS

| | | | |
|---|---|---|---|
| CN | 107088259 | A | 8/2017 |
| CN | 107334512 | A | 11/2017 |
| CN | 208756152 | U | 4/2019 |
| CN | 110267615 | A | 9/2019 |
| CN | 209392563 | U | 9/2019 |
| CN | 209885005 | U | 1/2020 |
| CN | 211434679 | U | 9/2020 |
| CN | 213031623 | U | 4/2021 |
| CN | 214050144 | U | 8/2021 |
| JP | 2011513004 | A | 4/2011 |
| JP | 2014512869 | A | 5/2014 |
| WO | 2009111712 | A1 | 9/2009 |
| WO | 2012109557 | A2 | 8/2012 |
| WO | 2019084442 | A1 | 5/2019 |

OTHER PUBLICATIONS

Chinese OA dated Sep. 29, 2021 issued in CN 201911164659.X.
Chinese OA dated Dec. 15, 2021 issued in CN 201911164659.X.
Chinese OA dated Mar. 29, 2022 issued in CN 202010525747.4.
Chinese OA dated Dec. 24, 2020 issued in CN 202021642528.6.
Chinese OA dated Jan. 15, 2021 issued in CN 202021642528.6.
Chinese OA dated Jul. 17, 2020 issued in CN 201922049775.9.
Chinese OA dated May 10, 2021 issued in CN 202021059439.9.
Notice of Reasons for Refusal dated Apr. 18, 2023 received in Japanese Patent Application No. JP 2022-526041.
Notice of Reasons for Refusal dated Oct. 13, 2023 received in Japanese Patent Application No. JP 2022-526041.
EP Communication date Jun. 30, 2025 in EP application No. 20892688.1.

* cited by examiner

BALLOON DEVICE AND A MEDICAL DEVICE COMPRISING IT

CROSS-REFERENCE TO RELATED APPLICATIONS

This application is a national phase entry of PCT International Application No. PCT/CN2020/108088, filed on Aug. 10, 2020, which claims priority to Chinese Patent Application No. 201911164659.X filed on Nov. 25, 2019 and Chinese Patent Application No. 202010525747.4 filed on Jun. 10, 2020. The disclosures of PCT International Application No. PCT/CN2020/108088 and Chinese Patent Application Nos. 201911164659.X and 202010525747.4 are incorporated by reference herein.

TECHNICAL FIELD

This application relates to the field of medical technology, in particular relates to a balloon device wherein the radial significant change part of the balloon device is coated with a pharmaceutical composition and a medical device comprising it.

BACKGROUND

Atrial septostomy is a mature technique in children with congenital heart disease and patients with advanced pulmonary hypertension. It has also achieved significant results in patients with diastolic dysfunction heart failure and those with systolic dysfunction and continuous increase of PCWP, but it has not been officially carried out clinically. The current study found that after atrial septostomy, regardless of whether stents are placed at the fistula, the fistula will heal naturally after 6 months, resulting in a great reduction of the surgical effect. Therefore, how to prevent the fistula from closing naturally in a short time is the key to ensure the final treatment effect of atrial septostomy.

SUMMARY

Cardiac drug balloon is a new technology. This technology makes drugs evenly distributed on the blood vessel wall through the implantation of paclitaxel coated special airbag, so as to inhibit the proliferation of vascular endothelium and smooth muscle, and prevent restenosis. Cardiac drug balloon can solve the problem of vascular stenosis without stent implantation, and is a new treatment method. However, all prior drug balloons are designed to prevent coronary artery and peripheral vascular endothelial hyperplasia, and there is no drug balloon specified for fistula, especially for the fistula of atrial septal with a thickness of only 2 to 3 mm.

This application discloses a balloon device for pharmaceutical delivery. Combined with the existing instruments to treat the fistula, it can realize the continuous opening of the atrial septal fistula and solve the problem of natural closure of the atrial septal fistula in a short time, so as to achieve the purpose of reducing cardiac preload and treating heart failure in a long time.

The technical scheme disclosed in this application includes the following embodiments:

Embodiment 1. A balloon device, comprising: a balloon catheter, and a balloon arranged on the balloon catheter, the balloon has a front end portion and a rear end portion in a longitudinal direction, and a pharmaceutical composition is provided on an outer surface of at least one of the front end portion and the rear end portion.

Embodiment 2. The balloon device according to embodiment 1, wherein the pharmaceutical composition is only provided on the outer surface of one of the front end portion and the rear end portion.

Embodiment 3. The balloon device according to embodiment 1, wherein the balloon catheter is provided with a guide wire through hole and a pressurized liquid channel, wherein the pressurized liquid channel is communicated with an interior of the balloon.

Embodiment 4. The balloon device according to embodiment 1, wherein the balloon is arranged at a front portion of the balloon catheter, and a distance between a front point of the balloon and a front point of the balloon catheter is about 5 to 20 mm.

Embodiment 5. The balloon device according to embodiment 1 or 2, wherein for the outer surface provided with the pharmaceutical composition, the pharmaceutical composition is only provided for a part with a radius greater than 2 mm, and the pharmaceutical composition is not provided on other outer surfaces of the balloon.

Embodiment 6. The balloon device according to embodiment 1, wherein a longitudinal section of the outer surface provided with the pharmaceutical composition has a concave arc shape, an circular arc shape, an elliptical arc shape, a parabola shape, a straight line shape, a broken line shape, an irregular curve shape, or a combination of two or more of them.

Embodiment 7. The balloon device according to embodiment 1, wherein the pharmaceutical composition comprises at least one of paclitaxel and rapamycin, and optionally, a drug carrier.

Embodiment 8. The balloon device according to any of embodiments 1-7, wherein a radial dimension of the balloon during expansion is 6-25 mm, such as 8 to 20 mm, such as 10 to 20 mm, such as 12 to 20 mm, such as 14 to 20 mm, such as 16 to 20 mm, such as 18 to 20 mm.

Embodiment 9. The balloon device according to any of embodiments 1-7, wherein the balloon is a non compliant balloon, a compliant balloon, or a semi compliant balloon.

Embodiment 10. A medical device, in particular for interventional treatment of percutaneous atrial septostomy, which comprises a balloon device according to any one of embodiments 1-9.

Embodiment 11. A balloon device, comprising: a balloon catheter, and a balloon arranged on the balloon catheter, the balloon has a concave area in the middle of the longitudinal direction when fully expanded, and a pharmaceutical composition is provided on the concave area.

Embodiment 12. The balloon device according to embodiment 11, wherein the balloon catheter is provided with a guide wire through hole and a pressurized liquid channel, wherein the pressurized liquid channel is communicated with an interior of the balloon.

Embodiment 13. The balloon device according to embodiment 11, wherein the pharmaceutical composition comprises at least one of paclitaxel and rapamycin, and optionally, a drug carrier.

Embodiment 14. The balloon device according to any of embodiments 11-13, wherein a radial dimension of the balloon during expansion is 6-25 mm, such as 8 to 20 mm, such as 10 to 20 mm, such as 12 to 20 mm, such as 14 to 20 mm, such as 16 to 20 mm, such as 18 to 20 mm.

Embodiment 15. The balloon device according to embodiment 14, wherein the minimum radial dimension of the concave area is less than 6 mm, for example, less than or equal to 5 mm.

Embodiment 16. The balloon device according to embodiment 15, wherein for the concave area provided with the pharmaceutical composition, the pharmaceutical composition is only provided for a part with a radius greater than 2 mm, and the pharmaceutical composition is not provided on other outer surfaces of the balloon.

In addition, the technical scheme disclosed in this application includes the following cases:

Case 1. A balloon device for pharmaceutical delivery, comprising: a balloon catheter, and a balloon arranged on the balloon catheter, the balloon has a concave arc shape in the longitudinal direction when fully expanded, and a pharmaceutical composition or a pharmaceutical composition layer is provided on an outer surface of an area of concave arc shape. The pharmaceutical composition layer has a thickness of about 1 micron to 100 microns, for example, 10 microns to 75 microns.

Case 2. The balloon device for pharmaceutical delivery according to case 1, wherein the concave arc shape is located in at least one selected from the group consisting of a longitudinal front portion of the balloon, a longitudinal middle portion of the balloon, and a longitudinal rear portion of the balloon.

Case 3. The balloon device for pharmaceutical delivery according to case 1, wherein the balloon catheter is provided with a guide wire through hole and a pressurized liquid channel, wherein the pressurized liquid channel is communicated with an interior of the balloon.

Case 4. The balloon device for pharmaceutical delivery according to case 1, wherein the balloon is arranged at a front portion of the balloon catheter, and a distance between a front point of the balloon and a front point of the balloon catheter is about 5 to 20 mm.

Case 5. The balloon device for pharmaceutical delivery according to case 1, wherein the concave arc shape is located in a longitudinal front portion of the balloon, and/or, a longitudinal rear portion of the balloon, the concave arc shape starts from portion near the balloon catheter to radial middle portion of the balloon radially.

Case 6. The balloon device for pharmaceutical delivery according to case 1, wherein the balloon has a longitudinal dimension and a radial dimension, the longitudinal dimension is ⅔ or less (½ or less) of the radial dimension, so that when the balloon is folded, most of the area with the concave arc shape is folded into the inner part, so as to avoid the loss of pharmaceutical composition during pushing process of the balloon device.

Case 7. The balloon device for pharmaceutical delivery according to case 1, wherein the pharmaceutical composition comprises at least one of paclitaxel and rapamycin, and optionally, a drug carrier. The drug carrier comprises a hydrophilic drug carrier.

Case 8. The balloon device for pharmaceutical delivery according to any of cases 1-7, wherein the balloon device comprises two balloons, the concave arc shape of one balloon is formed in the longitudinal front portion of the balloon, and the concave arc shape of the other balloon is formed in the longitudinal rear portion of the balloon.

Case 9. The balloon device for pharmaceutical delivery according to any of cases 1-8, wherein the balloon is a non compliant balloon, a compliant balloon, or a semi compliant balloon.

Case 10. A medical device, in particular for interventional treatment of percutaneous atrial septostomy, which comprises a balloon device according to any one of cases 1-9.

In addition, the technical scheme disclosed in this application includes the following schemes:

Scheme 1. A balloon device, comprising: a balloon catheter, and a balloon arranged on the balloon catheter, an outer surface of the balloon when deployed has at least one radial significant change part, and at least one of the radial significant change parts is provided with a pharmaceutical composition.

Scheme 2. The balloon device according to scheme 1, wherein only one of the radial significant change parts is provided with the pharmaceutical composition.

Scheme 3. The balloon device according to scheme 1, wherein the balloon catheter is provided with a guide wire through hole and a pressurized liquid channel, wherein the pressurized liquid channel is communicated with an interior of the balloon.

Scheme 4. The balloon device according to scheme 1, wherein the balloon is arranged at a front portion of the balloon catheter, and a distance between a front point of the balloon and a front point of the balloon catheter is about 5 to 20 mm.

Scheme 5. The balloon device according to scheme 1 or 2, wherein for the outer surface provided with the pharmaceutical composition, the pharmaceutical composition is only provided for a part with a radius greater than 2 mm, and the pharmaceutical composition is not provided on other outer surfaces of the balloon.

Scheme 6. The balloon device according to scheme 1, wherein the radial significant change part provided with the pharmaceutical composition is a front end surface of the balloon, a rear end surface of the balloon, or a middle surface of the balloon, a longitudinal section of the radial significant change part has a concave arc shape, an circular arc shape, an elliptical arc shape, a parabola shape, a straight line shape, a broken line shape, an irregular curve shape, or a combination of two or more of them.

Scheme 7. The balloon device according to scheme 1, wherein the pharmaceutical composition comprises at least one of paclitaxel and rapamycin, and optionally, a drug carrier.

Scheme 8. The balloon device according to any of schemes 1-7, wherein a radial dimension of the balloon during expansion is 6-25 mm, such as 8 to 20 mm, such as 10 to 20 mm, such as 12 to 20 mm, such as 14 to 20 mm, such as 16 to 20 mm, such as 18 to 20 mm.

Scheme 9. The balloon device according to any of schemes 1-7, wherein the balloon is a non compliant balloon, a compliant balloon, or a semi compliant balloon.

Scheme 10. A medical device, in particular for interventional treatment of percutaneous atrial septostomy, which comprises a balloon device according to any one of schemes 1-9.

Scheme 11. A method for treating the atrial septal fistula, comprising: contacting the radial significant change part provided with the pharmaceutical composition of the balloon device according to any one of schemes 1 to 9 with the atrial septal fistula, so as to administer the atrial septal fistula and its periphery.

Scheme 12. A method for treating the atrial septal fistula, comprising: contacting the radial significant change part provided with the pharmaceutical composition of the balloon device according to any one of schemes 1 to 9 with both sides of the atrial septal fistula, so as to delivery the pharmaceutical composition to the atrial septal fistula and its periphery of both sides.

The technical solution of the application, combined with the existing instruments (such as cutting balloon, etc.) to deal with the fistula, can realize the administration of the pharmaceutical composition to the atrial septal fistula and its periphery, especially can realize the continuous opening of the atrial septal fistula, solve the problem of natural closure of the atrial septal fistula in a short time, so as to achieve the purpose of reducing cardiac preload and treating heart failure in a long time.

BRIEF DESCRIPTION OF THE DRAWINGS

In order to more clearly explain the technical solution of the present disclosure, the accompanying drawings of the embodiment will be briefly introduced below. It is obvious that the accompanying drawings in the following description only refer to some embodiments of the present disclosure, rather than restrictions on the present disclosure.

Figure 1:
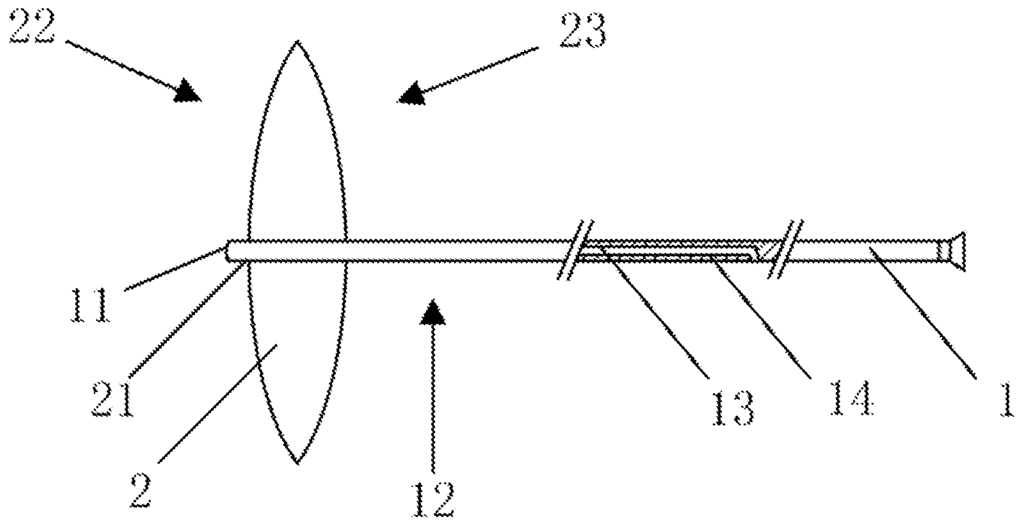
FIG. 1 shows a schematic view of the balloon device according to example 1.

Reference mark: 1—balloon catheter, 11—front point of the balloon catheter, 12—front portion of the balloon catheter, 13—guide wire through hole, 14—pressurized liquid channel, 2—balloon, 21—front point of the balloon, 22—front end portion of the balloon, 23—rear end portion of the balloon, 241—longitudinal front portion of the balloon, 242—longitudinal middle portion of the balloon, 243—longitudinal rear portion of the balloon, 25—concave arc shape, 251—portion near the balloon catheter, 252—radial middle portion, 26—concave area, 3—sleeve, 4—pharmaceutical composition or pharmaceutical composition layer.

DETAILED DESCRIPTION

In order to make the purpose, technical solutions and advantages of the embodiments of the present disclosure more clear, the technical scheme of the embodiments of the present disclosure will be clearly and completely described below in combination with the accompanying drawings of the embodiments of the present disclosure. Obviously, the described embodiments are part of the embodiments of the present disclosure, not all of the embodiments. Based on the described embodiments of the present disclosure, all other embodiments obtained by those skilled in the art without creative work belong to the scope of protection of the present disclosure.

The following terms in this application have specific meanings:

In this application, the direction along the catheter is defined as "longitudinal", and the direction perpendicular to the catheter is defined as "radial". The balloon is mainly expanded along the radial direction.

In this application, the portion that first reaches the area to be treated in the treatment is defined as "front", and the orientation opposite to "front" is defined as "rear".

In this application, "end", "portion" and "end portion" are used to describe different parts of the balloon and the balloon catheter, wherein "end" refers to a determined end point or end surface, "portion" is used to describe a certain range of areas, and "end portion" is used to describe a certain range of areas on the end surface.

For example, the "front point" of the balloon catheter means the end point or end surface of the balloon catheter which first reaches the area to be treated during operation, and the "front point" of the balloon means the end point or end surface of the balloon which first reaches the area to be treated during operation.

For example, the "front portion" of the balloon catheter refers to a certain range of the balloon catheter near the distal end of the operator, and the "longitudinal front portion", "longitudinal middle portion" and "longitudinal rear portion" of the balloon respectively refer to three areas within a certain range of the balloon body from the distal end to the proximal end for the operator in the direction of the balloon catheter. For example, the front portion refers to the front ¼, the rear portion refers to the rear ¼, and the middle portion refers to the area between the front ¼ and the rear ¼.

For example, the "front end portion" of the balloon refers to the end surface of the balloon which first reaches the area to be treated during operation, that is, the area from the front end point of the balloon to the radial farthest point of balloon when expanded. The "rear end portion" of the balloon refers to the portion opposite to the "front end portion", that is, the area from the radial farthest point of balloon when expanded to the rear endpoint of the balloon.

In this application, unless otherwise specified or different meanings can be obtained according to the understanding of the context, each term has the meaning commonly understood in the art.

This application discloses a balloon device and a medical device comprising it, wherein radial significant change part of the balloon device is coated with pharmaceutical composition. In this application, "radial significant change part" refers to the area where the radial dimension of the outer surface changes significantly with the change of the longitudinal dimension when the balloon is expanded. For example, the change rate of the radial dimension with the change of the longitudinal dimension is greater than 0.1, greater than 0.2, greater than 0.3, greater than 0.5, greater than 0.6, greater than 0.7, greater than 0.8, greater than 0.9, greater than 1, etc. Generally speaking, in this application, "radial significant change part" may comprises one or more selected from the group consisting of front end portion of the balloon, rear end portion of the balloon, and concave area in the longitudinal middle of the balloon.

On the one hand, this application discloses a balloon device wherein a end portion was provided with a pharmaceutical composition, comprises a balloon catheter, and a balloon arranged on the balloon catheter, wherein the balloon has a front end portion and a rear end portion in the longitudinal direction, and an outer surface of at least one of the front end portion and the rear end portion is coated with a pharmaceutical composition. Thus, when the front end portion or the rear end portion is in contact with the atrial septal fistula and its periphery, the pharmaceutical composition can directly act on the area to be treated, which is convenient to apply the pharmaceutical composition to the fistula and achieve better treatment effect. This application adopts common parameters in the art for the length of the balloon catheter. The diameter of the balloon catheter is generally 1.8 F-2.0 F. In some cases, it may also be selected in the range of 1.0 F to 6.0 F. The unit F here has the meaning generally understood by those skilled in the art. The diameter of the balloon catheter is 1 F, means the circumference of the balloon catheter is 1 mm. The diameter of the balloon catheter is 1.8 F, means the circumference of the balloon catheter is 1.8 mm. The diameter of the balloon catheter is 2.0 F, means the circumference of the balloon catheter is 2.0 mm.

In some embodiments, the pharmaceutical composition is provided on the outer surface of only one selected from the group consisting of the front end portion and the rear end portion. When the balloon is expanded in the heart, the outer surface of only one selected from the group consisting of the front end portion and the rear end portion is provided with a pharmaceutical composition which is applied to the fistula in the treatment. Compared with providing the pharmaceutical composition on the outer surface of both the front end portion and the rear end portion, this setting can minimize the amount of pharmaceutical composition released and reduce the side effects.

In some embodiments, the balloon catheter has a guide wire through hole and a pressurized liquid channel, wherein the pressurized liquid channel is communicated with the interior of the balloon. The setting of the guide wire through hole can make the balloon catheter reach the selected area for treatment along the guide wire under the guidance of the guide wire. The pressurized liquid channel is used to inject pressurized liquid into the balloon or extract pressurized liquid from the balloon. When the balloon reaches the target area, the pressurized liquid is injected into the pressurized liquid channel. Because of hydraulic pressure, the balloon is expanded. After the treatment of pharmaceutical delivery is completed, the pressurized liquid is extracted, and negative pressure is generated in the balloon, and the contraction and folding of the balloon is completed under the negative pressure. Generally, for accurate positioning, a marker (marker material) is also set inside the balloon, which is used to help the external device detect its position in the patient. In this application, there is no special restriction on the selection of markers, as long as the effect of accurate positioning of the balloon can be achieved.

In some embodiments, the balloon is arranged at the front portion of the balloon catheter, and the distance between the front point of the balloon and the front point of the balloon catheter is about 5 to 20 mm.

In some embodiments, at the outer surface provided with the pharmaceutical composition, the pharmaceutical composition is provided only for the part with a radius greater than 2 mm, and the pharmaceutical composition is not provided on other outer surfaces of the balloon. The "part with a radius greater than 2 mm" refers to the specific outer surface area of the front end portion and/or the rear end portion, and the vertical distance from any point in the specific outer surface area to the centerline of the catheter is greater than 2 mm. The pharmaceutical composition is only provided in the specific outer surface area, which coincides with the administration area of the fistula to be treated to maximize the contact area, improve the administration efficiency, delivery all the pharmaceutical composition to the fistula, realize the application of the minimum dose and reduce the toxicity caused by the pharmaceutical composition release in the non target area. It should be understood that the above range of setting the pharmaceutical composition is not a limitation on the balloon disclosed in this application. Those skilled in the art can select an appropriate range to set the pharmaceutical composition according to the actual needs, for example, select the radius range appropriate for coating the pharmaceutical composition on the outer surface of the end portion according to the fistula diameter, such as more than 2.5 mm, such as more than 3 mm, such as more than 3.5 mm, such as more than 4 mm. In the interventional treatment of atrial septostomy, the diameter of the fistula opening caused by cutting balloon with three fixed blades is about 5 mm, and the maximum diameter can be 12 mm in combination with other balloons. According to the clinical treatment experience of congenital heart disease, the target size can be reached when the diameter of the fistula opening is about 5 to 8 mm, which can effectively reduce the pressure of the left atrium.

The shape of the longitudinal section of the outer surface provided with the pharmaceutical composition is not particularly limited. In some embodiments, the longitudinal section of the outer surface provided with the pharmaceutical composition has a concave arc shape, an arc shape, an elliptical arc shape, a parabola shape, a straight line shape, a broken line shape, an irregular curve shape, or a combination of two or more of them. The "longitudinal section" in this application refers to the section along the direction of the catheter, and the "concave arc" refers to an arc surface having an depression direction opposite to the expansion direction of the balloon during expansion.

In some embodiments, the concave arc shape is formed in at least one of the longitudinal front portion, longitudinal rear portion and longitudinal middle portion of the balloon. Different settings of the concave arc shape can produce different treatment effects. When the concave arc shape is formed at the longitudinal front portion of the balloon, the area provided with the pharmaceutical composition can deal with one side of the atrial septum at the fistula, and cooperate with the balloon device with the concave arc shape formed in the longitudinal rear portion of the balloon, two sides of the atrial septum at the fistula can be processed. When the concave arc shape is formed in the longitudinal middle portion of the balloon, the area provided with the pharmaceutical composition can deal with both sides of the atrial septum at the fistula at the same time.

In some embodiments, the concave arc shape is formed at the longitudinal front portion and/or longitudinal rear portion of the balloon, and the concave arc shape starts from the portion near the balloon catheter and ends at the radial middle portion of the balloon. "portion near the balloon catheter" in this application refers to the range whose distance from the surface of the balloon catheter to the centerline of the balloon catheter is the radial first distance, and the radial first distance is about 1.5 mm to about 2.5 mm. When the concave arc shape is formed at the longitudinal front portion of the balloon, the longitudinal distance from the portion near the balloon catheter to the front point of the balloon catheter is preferably no more than 20 mm, and the longitudinal distance from the portion near the balloon catheter to the front end portion of the balloon is preferably 5 mm to 20 mm. In this application, "radial middle portion" refers to the area within a specific range with a vertical distance from the central line of the catheter from more than or equal to ¼ of the balloon radius to less than or equal to ¾ of the balloon radius when the balloon is fully expanded. In this application, "balloon radius" means that when the balloon is fully expanded, a vertical line perpendicular to the center line of the balloon catheter is made from the farthest point in the expanded radial direction, and the length of the vertical line is the balloon radius. It should be noted that "the concave arc shape starts from the portion near the balloon catheter and ends at the radial middle portion of the balloon" defines the range of the concave arc shape, which depends on the range of the target area of administration. In the interventional treatment of atrial septostomy, the expansion diameter of the fistula opening of the balloon is about 5 mm by cutting balloon with three fixed blades, and can be up to 12 mm in combination with other balloons. According to the clinical treatment experience of congenital heart disease, the target size is reached when the diameter of the fistula is about 5 to 8 mm, which can effectively reduce the pressure of the left atrium. The above size is not a limitation on the size of the balloon device disclosed in this application. Those skilled in the art can select an appropriate range of the concave arc shape according to the actual needs, for example, those skilled in the art can select an appropriate radial first distance according to the diameter of the fistula, and select an appropriate size of radial middle portion according to the target area of the pharmaceutical delivery, so as to achieve the best administration effect.

In a preferred embodiment, the radial first distance is 2.5 mm, and the radial distance between the radial middle portion and the centerline of the balloon catheter is 6.25 mm or more, such as 6.25 mm to 10 mm. The above dimensions are the preferred dimensions of the invention to solve technical problems and achieve the optimal treatment effect, rather than limiting the contents of this application.

In some embodiments, the balloon has a longitudinal dimension and a radial dimension, the longitudinal dimension is ⅔ or less (½ or less) of the radial dimension. In this application, when the balloon is fully expanded, the distance between the two longitudinal endpoints of the significant part of the balloon is a longitudinal dimension; the distance between the two ends of the balloon in the radial direction is a radial dimension, which is usually twice the radius of the balloon. The significant part mentioned here refers to the part on the balloon whose radial distance is greater than ¼ of the balloon radius. The distance between the two longitudinal endpoints of the significant part of the balloon refers to the distance between the front end and the rear end of the part on the balloon whose radial distance is greater than ¼ of the balloon radius. On the one hand, such size design makes most or all of the area with the concave arc shape folded into the interior when the balloon is folded, so as to avoid the loss of the pharmaceutical composition due to dissolution during the pushing process of the balloon device. On the other hand, the balloon device disclosed in the application is mainly used to solve the technical problem of natural closure of the atrial septal fistula. The area to be treated is a plane within a certain range around the fistula. Such a size design makes the balloon is in a flat shape in the longitudinal direction when fully expanded, so as to adapt to the internal space of the heart and produce sufficient drug delivery area. As a general arrangement of this application, the longitudinal dimension of the balloon is generally 5 mm to 16 mm, for example, 7.5 mm to 13 mm. As a general arrangement of this application, the radial dimension of the balloon is generally 10 mm to 25 mm, for example, 15 mm to 20 mm.

In some embodiments, the longitudinal section of the outer surface provided with the pharmaceutical composition does not have a concave arc shape. For example, the longitudinal section of the outer surface provided with the pharmaceutical composition has an arc shape, an elliptical arc shape, a parabola shape, a straight line shape, a broken line shape, an irregular curve shape, or a combination of two or more of them. The circular arc shape, elliptical arc shape and parabola shape described in this application refer to the convex shape of the balloon in the same expansion direction as the balloon during expansion, and do not include concave arc shape. The different shapes of the longitudinal section of the outer surface of the pharmaceutical composition can produce different fitting effects between the end of the balloon and the fistula and the area around the fistula. Those skilled in the art can select different balloons according to the surface shape of the fistula and the area around the fistula.

In some embodiments, the pharmaceutical composition contains at least one of paclitaxel and rapamycin, and optionally, a drug carrier. The drug carrier is preferably comprised of a hydrophilic drug carrier and/or a hydrophobic drug carrier. In some embodiments, the hydrophilic drug carrier is at least one selected from iopamidol and Iopromide. The existing drug coated balloon (DCB) interventional therapy technology attaches the drug that inhibits cell proliferation to the surface of the balloon. By expanding the balloon, the drug coated surface is attached to the atrial septal fistula and around its periphery, and the drug is delivered to the target area, so as to achieve the effect of inhibiting smooth muscle proliferation. Paclitaxel and rapamycin have the effect of inhibiting cell proliferation and are widely used in the field of coronary artery and peripheral interventional therapy in clinic. Both of them are lipophilic drugs. The lipophilic drugs paclitaxel and/or rapamycin and the hydrophilic drug carrier ioparol and/or iopromide are arbitrarily combined to form the pharmaceutical composition. The hydrophilic drug carrier can form a porous coating with high contact surface between lipophilic drug molecules and blood vessel wall, enhance the dissolution and release of lipophilic drug molecules, and may change drug delivery and its interaction with tissue. The pharmaceutical composition is loaded on the surface of the front end portion and/or rear end portion of the balloon device disclosed in this application as a balloon coating. After the balloon is expanded, the front end portion and/or rear end portion loaded with the pharmaceutical composition is in full contact with the area to be treated, and the target drug dose is released uniformly and rapidly. Clinical experience showed that only a short time of contact of 30 seconds to 70 seconds is enough to inhibit cell proliferation, and prevent the creeping of surrounding endothelium and the natural healing of fistula.

In some embodiments, the radial dimension of the balloon at the time of expansion is 6-25 mm, such as 8 to 20 mm, such as 10 to 20 mm, such as 12 to 20 mm, such as 14 to 20 mm, such as 16 to 20 mm, such as 18 to 20 mm. In this application, when the balloon is expanded, the distance between the two end points in the radial direction is the radial size, and the radial size determines the size of the drug loading area. Those skilled in the art can select the appropriate radial size according to the range of the area to be treated around the fistula. In addition, larger radial size can ensure that the drug composition loaded at the end of the balloon is wrapped on the inner side when the balloon is folded, so as to avoid the loss of drugs due to dissolution during the pushing process of the balloon device.

In some embodiments, the balloon is a non compliant balloon, a compliant balloon, or a semi compliant balloon. The compliance of the balloon described in this application refers to the characteristics of the corresponding changes in the shape or volume of the balloon with each increase in atmospheric pressure (atm) when the balloon is fully filled, and is an indicator of the balloon tensile capacity. The three different types of balloon used in this application have different characteristics: the balloon diameter of the compliant balloon increases with the increase of pressure, and disperses the expansion pressure. the balloon diameter of a non compliant balloon remains unchanged after reaching the specified size no matter how much pressure is applied to non compliant balloon. The non compliant balloon focuses the expansion pressure on the treatment site, and has weak adaptability to blood vessels. The semi compliant balloon has a wide working range and the balloon size can be flexibly manipulated, which is mostly used for pre expansion. In practical application, those skilled in the art can select different balloons according to actual needs to achieve the best technical effect. The materials and methods for making the balloon device are not particularly limited, and those skilled in the art can choose the material and method for making the balloon device according to actual needs.

Another aspect of this application provides a medical device comprising a balloon device according to any one of the other embodiments described in this application. Specifically, another aspect of the present application provides a medical device for interventional treatment of percutaneous atrial septostomy, which includes a balloon device according to any one of the other embodiments described in the present application.

The application also discloses a balloon device, which comprises a balloon catheter and a balloon arranged on the balloon catheter. When fully expanded, the balloon has a concave area in the longitudinal middle portion, and the outer surface of the concave area is provided with a pharmaceutical composition. In this application, by setting a concave area in the middle portion of the longitudinal direction and setting a pharmaceutical composition on the outer surface of the concave area, the pharmaceutical composition can act directly on the area to be treated through the contact between the concave area of the balloon and the fistula, so as to apply drugs to the fistula and achieve better treatment effect.

In some embodiments, the balloon catheter of the balloon device has a guide wire through hole and a pressurized liquid channel, wherein the pressurized liquid channel is communicated with the interior of the balloon. The setting of the guide wire through hole can make the balloon catheter reach the selected area for treatment along the guide wire under the guidance of the guide wire. The pressurized liquid channel is used to inject pressurized liquid into the balloon or extract pressurized liquid from the balloon. When the balloon reaches the target area, the pressurized liquid is injected into the pressurized liquid channel. Because of hydraulic pressure, the balloon is expanded. After the treatment is completed, the pressurized liquid is extracted, and negative pressure is generated in the balloon, and the contraction and folding of the balloon is completed under the negative pressure. Generally, for accurate positioning, a marker (marker material) is also set inside the balloon, which is used to help the external device detect its position in the patient. In this application, there is no special restriction on the selection of markers, as long as the effect of accurate positioning of the balloon can be achieved.

In some embodiments, the pharmaceutical composition of the balloon device contains at least one of paclitaxel and rapamycin, and optionally, a drug carrier. The drug carrier is preferably comprised of a hydrophilic drug carrier and/or a hydrophobic drug carrier. In some embodiments, the hydrophilic drug carrier is at least one selected from iopamidol and Iopromide. The existing drug coated balloon (DCB) interventional therapy technology attaches the drug that inhibits cell proliferation to the surface of the balloon. By expanding the balloon, the drug coated surface is attached to the atrial septal fistula and around its periphery, and the drug is delivered to the target area, so as to achieve the effect of inhibiting smooth muscle proliferation. Paclitaxel and rapamycin have the effect of inhibiting cell proliferation and are widely used in the field of coronary artery and peripheral interventional therapy in clinic. Both drugs are lipophilic drugs. The lipophilic drugs paclitaxel and/or rapamycin and the hydrophilic drug carrier ioparol and/or iopromide are arbitrarily combined to form the pharmaceutical composition. The hydrophilic drug carrier can form a porous coating with high contact surface between lipophilic drug molecules and blood vessel wall, enhance the dissolution and release of lipophilic drug molecules, and may change drug delivery and its interaction with tissue. The pharmaceutical composition is loaded on the surface of the front end portion and/or rear end portion of the balloon device disclosed in this application as a balloon coating. After the balloon is expanded, the front end portion and/or rear end portion provided with the pharmaceutical composition is fully contacted with the area to be treated, and the target drug dose is released uniformly and rapidly. Clinical experience shows that contacting only a short time of 30 seconds to 70 seconds is enough to inhibit cell proliferation, and prevent the creeping of surrounding endothelium and the natural healing of fistula.

In some embodiments, the radial dimension of the balloon at the time of expansion is 6-25 mm, such as 8 to 20 mm, such as 10 to 20 mm, such as 12 to 20 mm, such as 14 to 20 mm, such as 16 to 20 mm, such as 18 to 20 mm.

In some embodiments, the minimum radial dimension of the concave area of the balloon device used for drug administration is less than 6 mm, for example, less than or equal to 5 mm. In this application, the concave area is provided with the pharmaceutical composition, and its minimum radial size should not exceed the diameter of the fistula. Those skilled in the art can select an appropriate radial size according to the diameter of the fistula to achieve the best administration effect.

In some embodiments, the pharmaceutical composition is provided only on the outer surface of the concave area of the balloon device with a radius greater than 2 mm, and the pharmaceutical composition is not provided on other outer surfaces of the balloon. The “part with a radius greater than 2 mm” refers to the specific outer surface area of the longitudinal middle portion, and the vertical distance from any point in the specific outer surface area to the centerline of the catheter is greater than 2 mm. The pharmaceutical composition is only provided on the specific outer surface area, which coincides with the administration area of the fistula to be treated to maximize the contact area, improve the administration efficiency, act all the pharmaceutical composition on the fistula, realize the application of the minimum dose and reduce the toxicity caused by the pharmaceutical composition release in the non target area. It should be understood that the above range of setting the pharmaceutical composition is not a limitation on the balloon disclosed in this application. Those skilled in the art can select an appropriate range to set the pharmaceutical composition according to the actual needs, for example, select the radius appropriate for coating according to the fistula diameter, such as more than 2.5 mm, such as more than 3 mm, such as more than 3.5 mm, such as more than 4 mm.

In this application, the materials and methods for making the balloon device are not particularly limited, as long as they can meet the specific operation requirements.

The balloon and balloon catheter can be made by polyamide (such as nylon 66, nylon 12, etc.) and polyether amide block copolymer. The method for making balloon catheter can adopt various known methods in the prior art. The balloon can be formed by blow molding. A marker material is arranged at the catheter located in the balloon, and the marker material is usually platinum iridium alloy. The balloon and catheter can be bonded together by hot melting or with appropriate adhesive.

This application also discloses a method for treating the atrial septal fistula, which comprises: contacting the balloon of the balloon device with the atrial septal fistula, so as to delivery the pharmaceutical composition to the atrial septal fistula and its periphery. The position where contacts the fistula is the position where the pharmaceutical composition is coated on the balloon.

In some embodiments, the method also includes delivery the pharmaceutical composition to both sides of the atrial septal fistula. For example, the pharmaceutical composition is delivered to both sides of the atrial septum through a balloon device wherein the pharmaceutical composition is coated on the front end portion and a balloon device wherein the pharmaceutical composition is coated on the rear end portion.

The content described above can be used alone or in combination. Through the following embodiments, this application can be more easily understood.

EXAMPLES

Example 1 [Circular Arc Shape, the Pharmaceutical Composition was Coated on the Front End Portion]

As shown in FIG. 1, the application disclosed a balloon device wherein the pharmaceutical composition was coated on the front end portion of the balloon (i.e. an end coated balloon device), the balloon device was comprised of a balloon catheter 1 and a balloon 2. The balloon 2 was arranged at the front portion 12 of the balloon catheter. The distance between the front point 21 of the balloon and the front point 11 of the balloon catheter was 5 mm. The balloon 2 had a front end portion 22 and a rear end portion 23 in the longitudinal direction. The longitudinal section of the outer surfaces of the front end portion 22 and the rear end portion 23 had a circular arc shape. The radial dimension of the balloon 2 during expansion was 18 mm. The diameter of the balloon catheter 1 was 1.8 F. The balloon catheter 1 was provided with a guide wire through hole 13 and a pressurized liquid channel 14, wherein the pressurized liquid channel 14 was communicated with the interior of the balloon 2.

Figure 2:
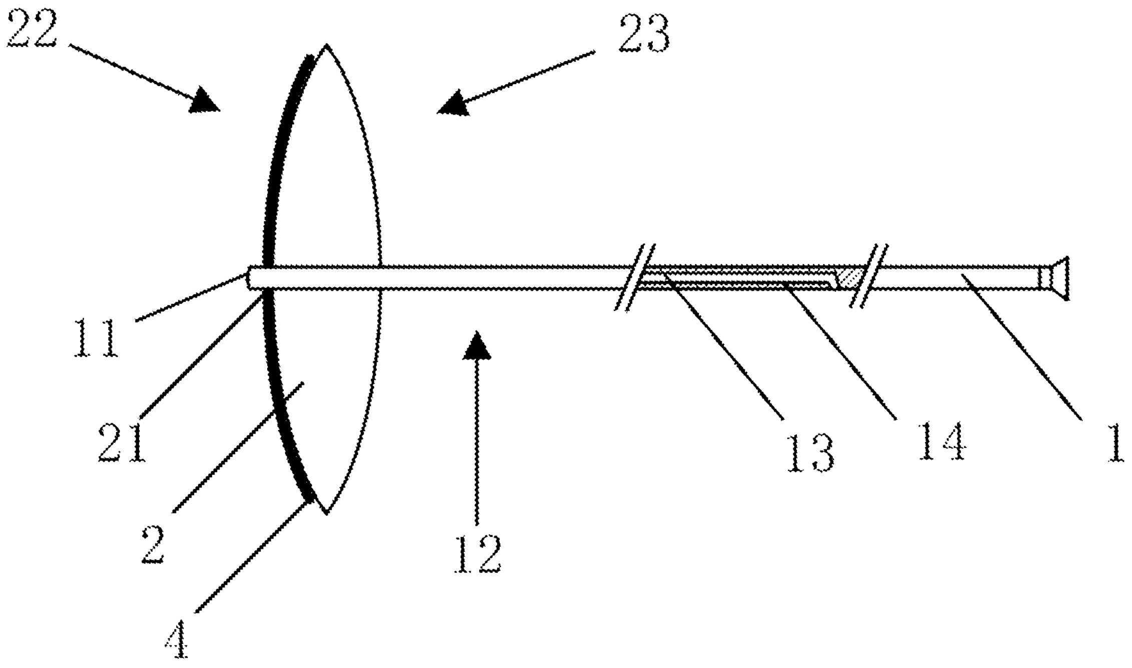
FIG. 2 shows a schematic view of the balloon device wherein the pharmaceutical composition is provided at the front end portion of the balloon according to example 1.

As shown in FIG. 2, the outer surface of the front end portion 22 of the balloon 2 was provided with a pharmaceutical composition 4, which was paclitaxel and iopromide. The pharmaceutical composition 4 was formed into a pharmaceutical composition layer with a thickness of about 50 microns.

In the treatment, the guide wire was firstly set, wherein the guide wire was penetrated through the atrial septum of a heart. A fistula of appropriate size on the atrial septum of the heart was created. Then, the end coated balloon device was set at the fistula along with the guide wire. The front portion 12 of the balloon catheter was pushed to the far end and reached the target area by PTCA (Percutaneous Transluminal Coronary Angioplasty) technology, then pressurized fluid was injected into the balloon 2 through the pressurized fluid channel 14. Under the hydraulic pressure, the balloon 2 was fully expanded, and the internal pressure in the balloon 2 was maintained. The surface of the front end portion 22 of the balloon 2 was in full contact with one side of the atrial septum at the fistula to be treated, and the pharmaceutical composition was quickly released to the contact area. After reaching the predetermined expansion time, the pressurized liquid was drawn out, and the balloon 2 was deflated and the balloon device was withdrawn to complete the treatment.

Example 2 [Circular Arc Shape, the Pharmaceutical Composition was Coated on the Rear End Portion]

Figure 3:
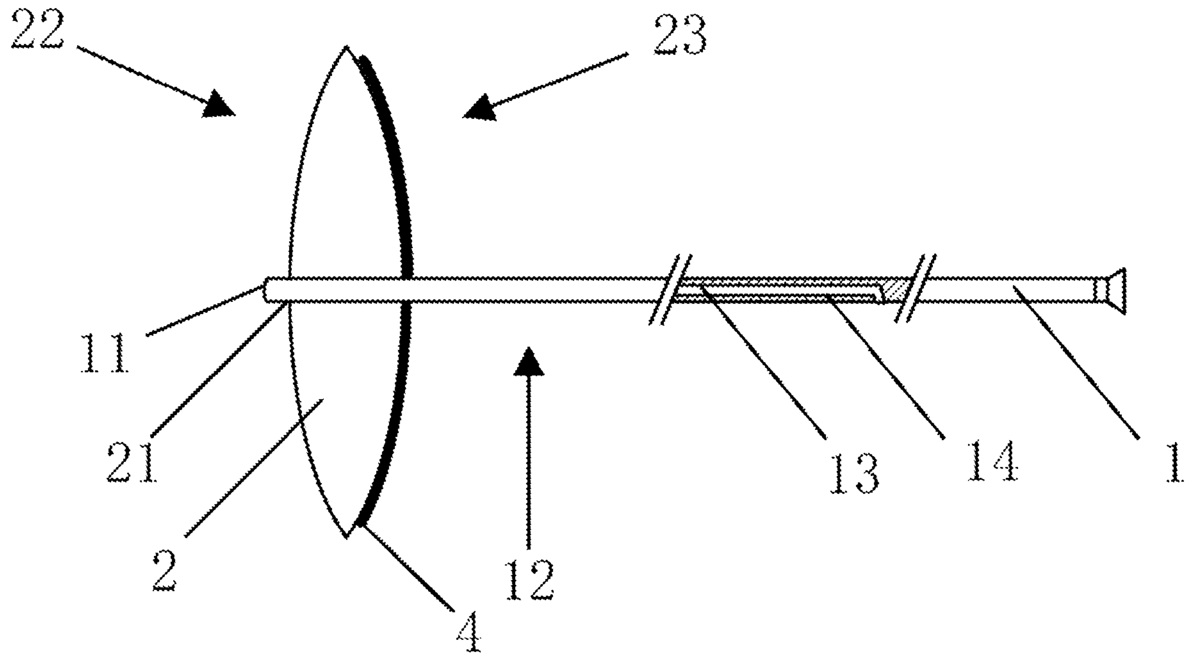
FIG. 3 shows a schematic view of the balloon device wherein the pharmaceutical composition is arranged at the rear end portion of the balloon according to example 2.

The end coated balloon device disclosed in example 2 was shown in FIG. 3, and its structure was the same as that in example 1, except that the outer surface of the rear end portion 23 of the balloon 2 in example 2 was provided with a pharmaceutical composition 4.

In the treatment, the guide wire was firstly set, wherein the guide wire was penetrated through the atrial septum of a heart. A fistula of appropriate size on the atrial septum of the heart was created. Then, the end coated balloon device was set at the fistula along with the guide wire. The front portion 12 of the balloon catheter was pushed to the far end and reached the target area through the fistula by PTCA technology, then pressurized fluid was injected into the balloon 2 through the pressurized fluid channel 14. Under the hydraulic pressure, the balloon 2 was fully expanded, and the internal pressure in the balloon 2 was maintained. The surface of the rear end portion 23 of the balloon 2 was in full contact with one side of the atrial septum at the fistula to be treated, and the pharmaceutical composition was quickly released to the target area. After reaching the predetermined expansion time, the pressurized liquid was drawn out, and the balloon 2 was deflated and the balloon device was withdrawn to complete the treatment.

Example 3 [Circular Arc Shape, the Pharmaceutical Composition was Coated on Both the Front End Portion and the Rear End Portion, this Example is a Combination of Example 1 and Example 2]

The end coated balloon device disclosed in example 3 was a combination of the balloon device disclosed in example 1 and the balloon device disclosed in example 2, wherein the outer surface of the front end portion 22 of balloon device 1 (i.e. the balloon device disclosed in example 1) was provided with the pharmaceutical composition 4, and the outer surface of the rear end portion 23 of balloon device 2 (i.e. the balloon device disclosed in example 2) was provided with the pharmaceutical composition 4. The pharmaceutical composition 4 comprised paclitaxel, rapamycin and iopamidol.

In the treatment, the front portion 12 of the balloon catheter of the balloon device 1 was pushed to the far end in the same way as in example 1 to reach the target area that does not pass through the fistula, so that the surface of the front end portion 22 was in full contact with the side of the atrial septum at the fistula to be treated. The balloon device 1 was withdrawn after the treatment was completed. Then, the front portion 12 of the balloon catheter of the balloon device 2 was pushed to the far end in the same way as in example 2, and reached the target area through the fistula, so that the surface of the rear end portion 23 was in full contact with the other side of the atrial septum at the fistula to be treated. The balloon device 2 was withdrawn after the treatment was completed. Thus, the treatment of the two sides of the atrial septum at the fistula was completed in turn. It should be noted that during each treatment, the fistula itself can also be treated with the pharmaceutical composition.

Example 4 [Circular Arc Shape, the Pharmaceutical Composition was Coated on Part of the Front End Portion]

Figure 4:
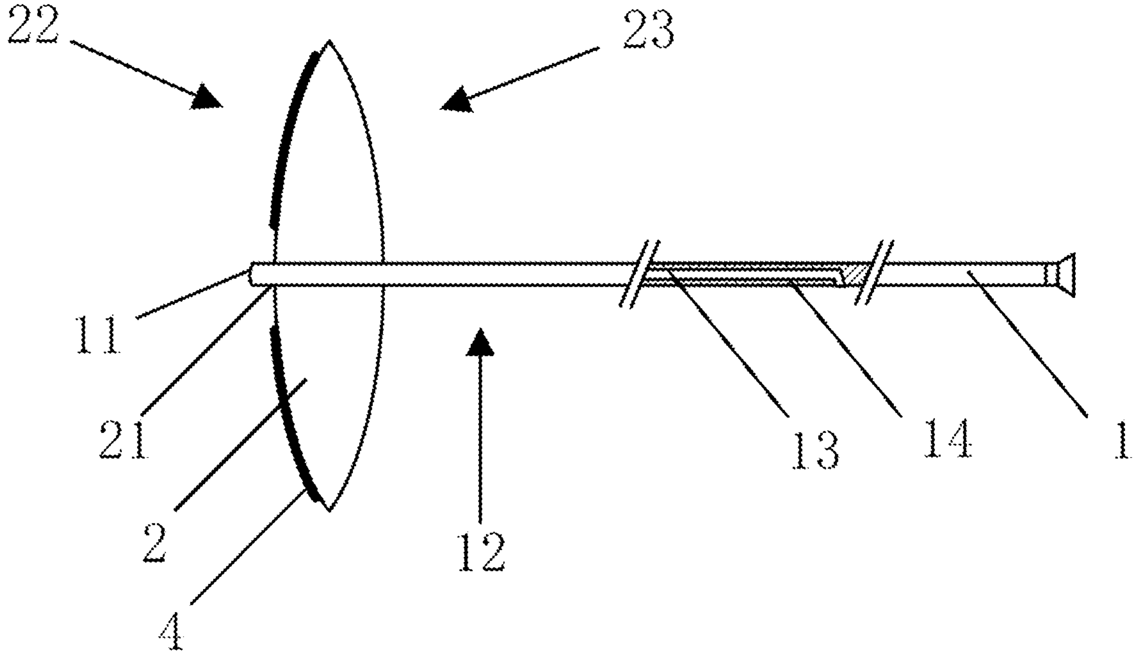
FIG. 4 shows a schematic view of the balloon device according to example 4.

The end coated balloon device disclosed in this example was shown in FIG. 4, and its structure was the same as that in example 1, except that the pharmaceutical composition 4 was only coated on the part with a radius greater than 3 mm of the front end portion.

The operation method of using the balloon device disclosed in this example was consistent with that in example 1. The drug coated end disclosed in this example was coincided with the drug administration area of the fistula to be treated to maximize the contact area, improve the drug administration efficiency, and act all the drugs on the fistula, which could achieve the minimum dose of drug application and reduce the toxicity caused by drug release in the non target area.

Example 5 [the Longitudinal Section of the Front End Portion had a Linear Shape, the Longitudinal Section of the Rear End Portion had an Elliptical Arc Shape, and Part of the Front End Portion was Coated with Pharmaceutical Composition]

Figure 5:
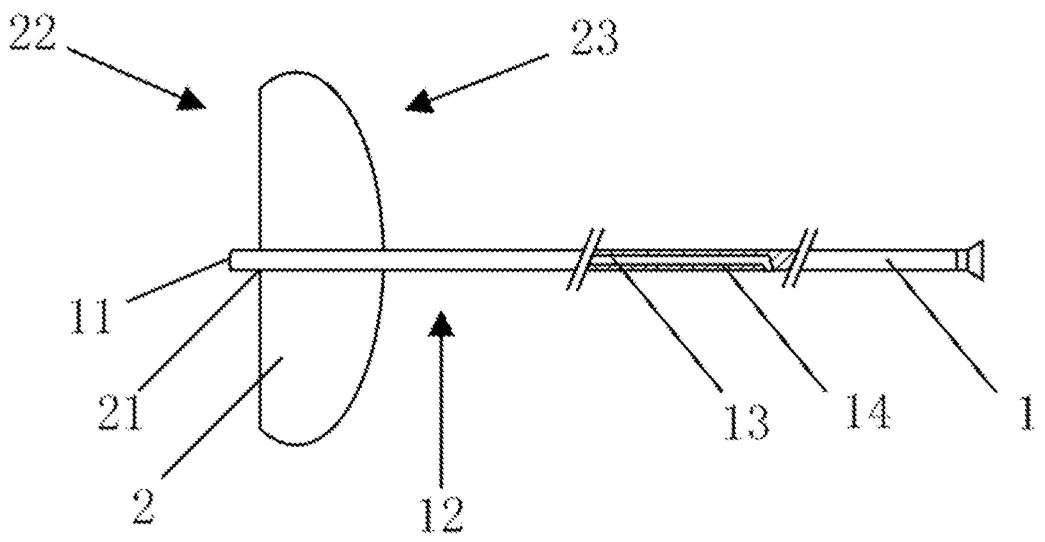
FIG. 5 shows a schematic view of the balloon device according to example 5.

The end coated balloon device disclosed in this example was shown in FIG. 5, and its structure was basically consistent with that in example 1. The difference was that the longitudinal section of the outer surface of the front end portion 22 had a linear shape, and the longitudinal section of the outer surface of the rear end portion 23 had an elliptical arc shape. The pharmaceutical composition (not shown in the figure) was provided only at the part with a radius greater than 3 mm at the outer surface of the front end portion 22.

In the treatment, the operation method was consistent with that in example 1.

Example 6 [the Longitudinal Section of the Front End Portion had an Elliptical Arc Shape, the Longitudinal Section of the Rear End Portion had a Circular Arc Shape, and Part of the Front End Portion was Coated with Pharmaceutical Composition]

Figure 6:
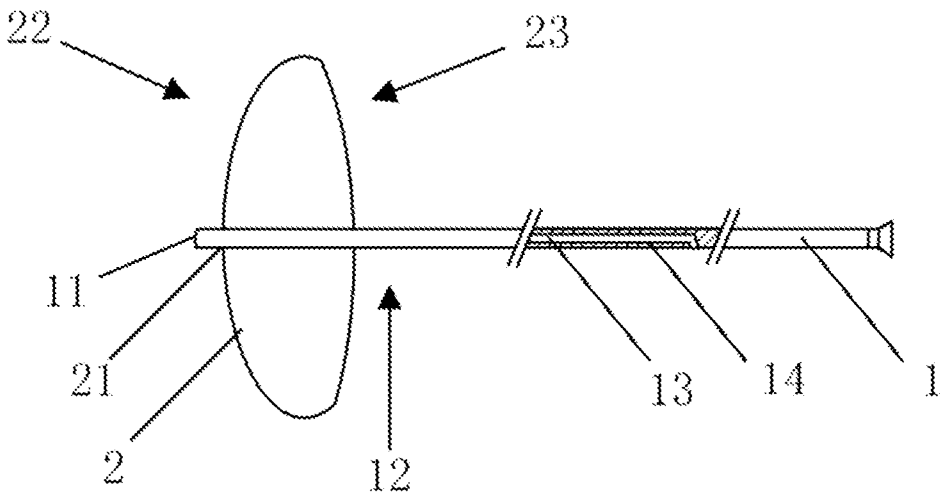
FIG. 6 shows a schematic view of the balloon device according to example 6.

The end coated balloon device disclosed in this example is shown in FIG. 6, and its structure is basically the same as that in example 1, except that the longitudinal section of the outer surface of the front end portion 22 had an elliptical arc shape, and the longitudinal section of the outer surface of the rear end portion 23 had a circular arc shape. The pharmaceutical composition (not shown in the figure) is provided only at the part with a radius greater than 3 mm at the outer surface of the rear end portion 23.

In the treatment, the operation method was consistent with that in example 2.

Example 7 [the Longitudinal Sections of Both the Front End Portion and the Rear End Portion had an Elliptical Arc Shape]

Figure 7:
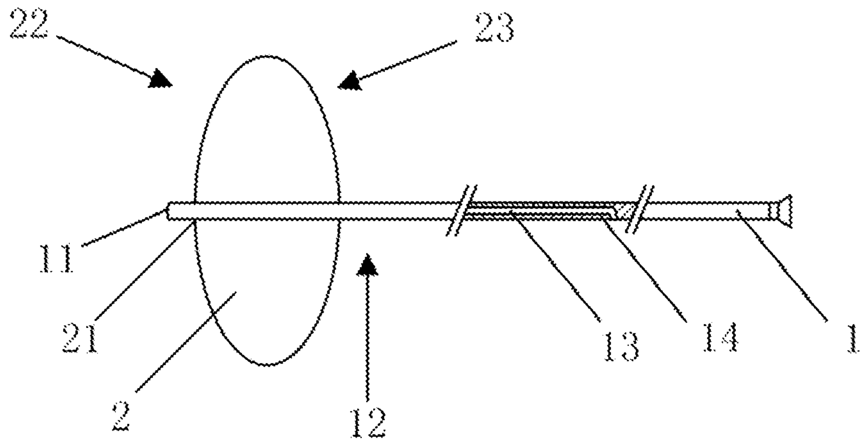
FIG. 7 shows a schematic view of the balloon device according to example 7.

The end coated balloon device disclosed in this example was shown in FIG. 7, and its structure was basically the same with that in example 1, except that the longitudinal sections of both the outer surfaces of the front end portion 22 and the rear end portion 23 had an elliptical arc shape.

The setting of the pharmaceutical composition (not shown in the figure) and treatment method could adopt any of examples 1 to 4.

Example 8 [the Longitudinal Sections of Both the Front End Portion and the Rear End Portion was a Combination of Linear Shape and Circular Arc Shape]

Figure 8:
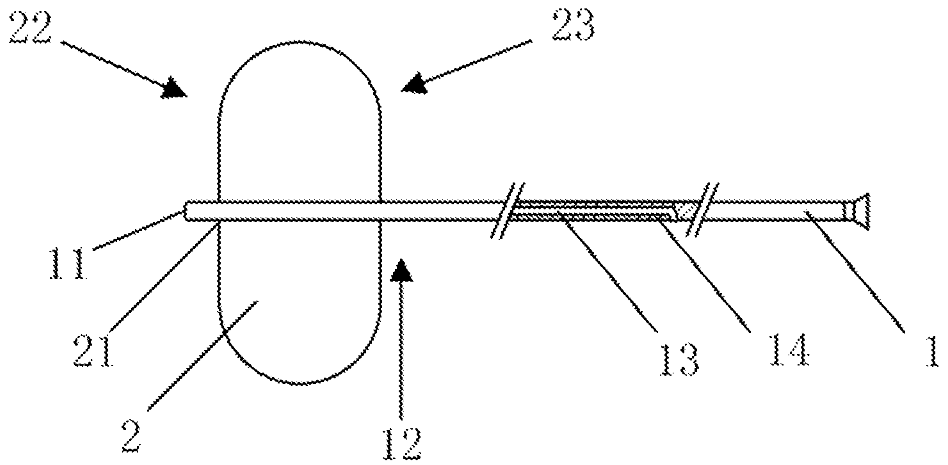
FIG. 8 shows a schematic view of the balloon device according to example 8.

The end coated balloon device disclosed in this example was shown in FIG. 8, and its structure was basically the same as that in example 1, except that the longitudinal sections of the outer surfaces of both the front end portion 22 and the rear end portion 23 were a combination of linear shape and circular arc shape.

The setting of the pharmaceutical composition (not shown in the figure) and treatment method could adopt any of examples 1 to 4.

Example 9 [the Longitudinal Sections of Both the Front End Portion and the Rear End Portion had a Trapezoid Shape]

Figure 9:
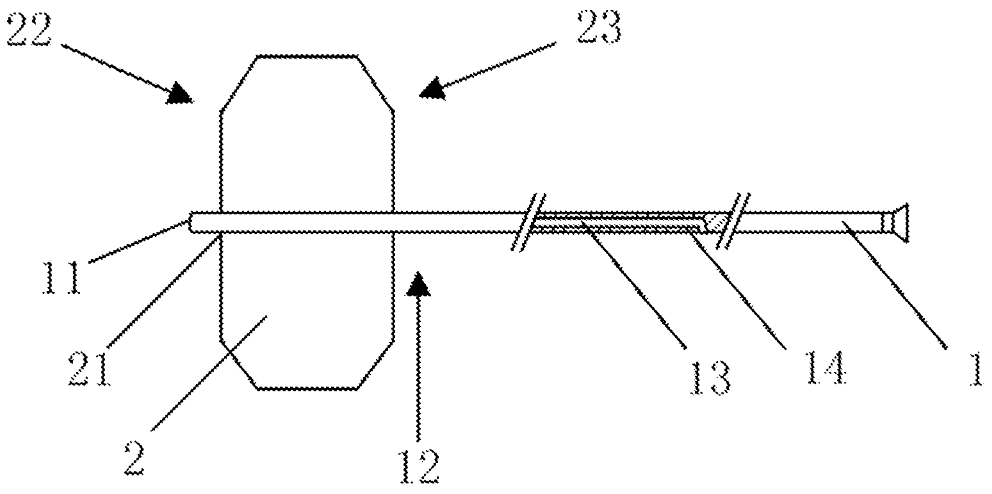
FIG. 9 shows a schematic view of the balloon device according to example 9.

The end coated balloon device disclosed in this example was shown in FIG. 9, and its structure was basically the same as that in example 1, except that the longitudinal sections of the outer surfaces of both the front end portion 22 and the rear end portion 23 had a trapezoid shape.

The setting of the pharmaceutical composition (not shown in the figure) and treatment method could adopt any of examples 1 to 4.

Example 10 [the Longitudinal Sections of Both the Front End Portion and the Rear End Portion had a Broken Line Shape]

Figure 10:
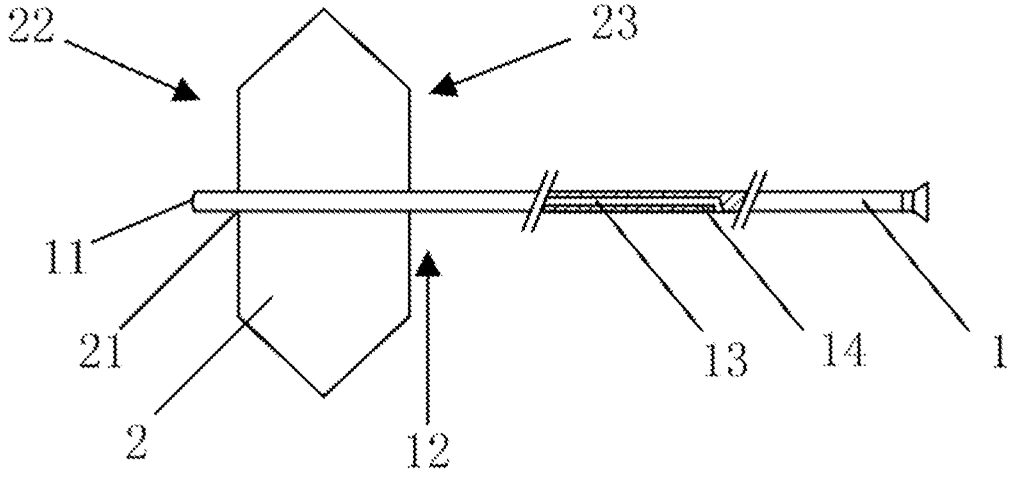
FIG. 10 shows a schematic view of the balloon device according to example 10.

The end coated balloon device disclosed in this example was shown in FIG. 10, and its structure was basically the same with that in example 1, except that the longitudinal sections of both the outer surfaces of the front end portion 22 and the rear end portion 23 had a broken line shape.

The setting of the pharmaceutical composition (not shown in the figure) and treatment method could adopt any of examples 1 to 4.

Example 11 [the Concave Arc Shape is Located in the Longitudinal Front Portion of the Balloon]

Figure 11:
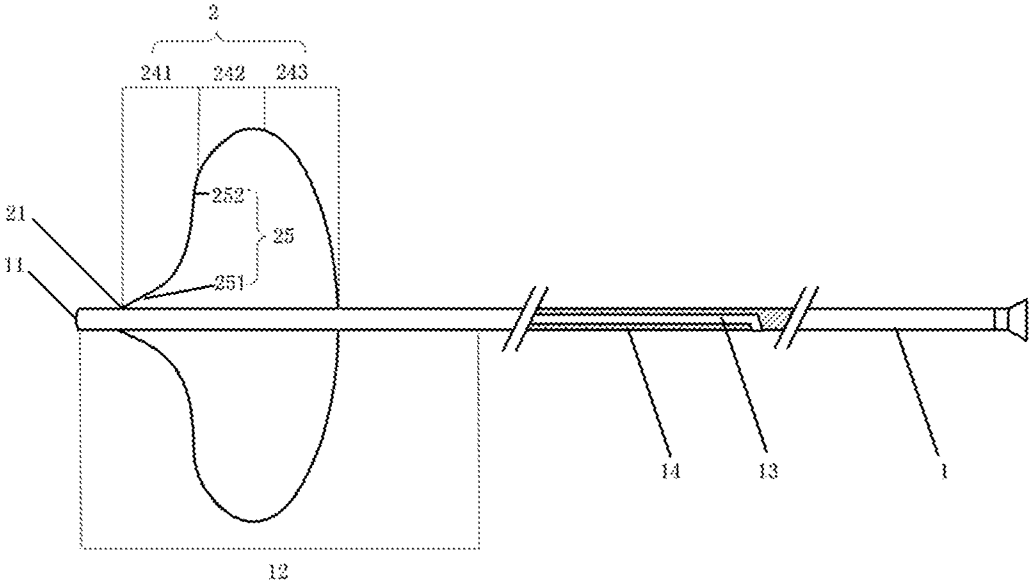
FIG. 11 shows a schematic view of the balloon device according to example 11.

The balloon device disclosed in this example was comprised of a balloon catheter 1 and a balloon 2. FIG. 11 showed the structure of the balloon device when fully expanded, and the balloon 2 was arranged at the front portion 12 of the balloon catheter. The diameter of the balloon catheter 1 was 1.8 F. The interior of the balloon catheter 1 was provided with a guide wire through hole 13 and a pressurized liquid channel 14. The pressurized liquid channel 14 was communicated with the interior of the balloon 2. The balloon 2 was comprised of a longitudinal front portion 241, a longitudinal middle portion 242 and a longitudinal rear portion 243.

When fully expanded, the balloon 2 had a longitudinal dimension of 10 mm and a radial dimension of 15 mm, and its longitudinal section which was located at the longitudinal front portion 241 had a concave arc shape 25. The concave arc shape 25 started from portion near the balloon catheter 251 to radial middle portion 252 of the balloon radially. The radial distance between the portion near the balloon catheter 251 and the centerline of the balloon catheter 1 was 2 mm, and the radial distance between the radial middle portion 252 and the centerline of the balloon catheter 1 was 3.75 mm [Here, the balloon 2 was fully expanded, and had a radial dimension of 15 mm, and radius of the balloon 2 was 7.5 mm]. The longitudinal distance from the portion near the balloon catheter 251 to the front point of the balloon catheter was 20 mm, and the longitudinal distance from the portion near the balloon catheter 251 to the front point of the balloon was 10 mm.

Figure 12:
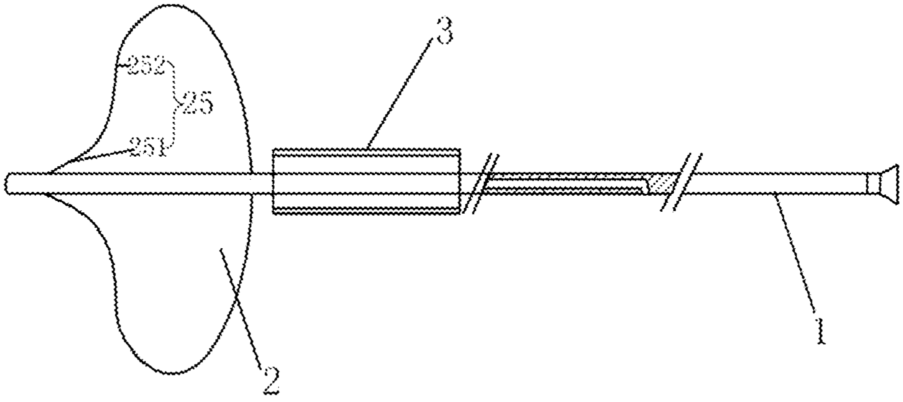
FIG. 12 shows a schematic view of the folding of the balloon device according to example 11.

As shown in FIG. 12, when folding the balloon 2, the sleeve 3 with an inner diameter of 5 mm was sleeved from the back side area of the concave arc shape 25, and the filling fluid (gas or liquid) inside the balloon 2 was evacuated at the same time, so that the area of the concave arc shape 25 could be embedded in the folded balloon 2, and most of the area of the concave arc shape 25 was folded inside.

Figure 13:
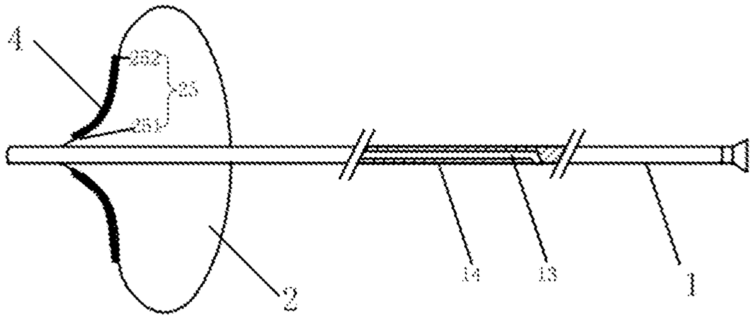
FIG. 13 shows a schematic view of the balloon device wherein the concave arc shape is coated with pharmaceutical composition according to example 11.

As shown in FIG. 13, the surface of the concave arc shape 25 was provided with a pharmaceutical composition 4, which comprised paclitaxel and iopromide. The pharmaceutical composition was formed into a pharmaceutical composition layer 4 with a thickness of about 50 microns. In the treatment, the guide wire was firstly set, wherein the guide wire was penetrated through the atrial septum of a heart. A fistula of appropriate size on the atrial septum of the heart was created. Then, the balloon device for pharmaceutical delivery was set at the fistula along with the guide wire. The front portion 12 of the balloon catheter was pushed to the far end and reached the target area by PTCA (Percutaneous Transluminal Coronary Angioplasty) technology, then pressurized fluid was injected into the balloon 2 through the pressurized fluid channel 14. Under the hydraulic pressure, the balloon 2 was fully expanded, and the internal pressure in the balloon 2 was maintained. The surface of the front end portion 22 of the balloon 2 was in full contact with one side of the atrial septum at the fistula to be treated, and the pharmaceutical composition was quickly released to the contact area. After reaching the predetermined expansion time, the pressurized liquid was drawn out, and the balloon 2 was deflated and the balloon device was withdrawn to complete the treatment.

Example 12 [the Concave Arc Shape was Located at the Longitudinal Rear Portion of the Balloon]

Figure 14:
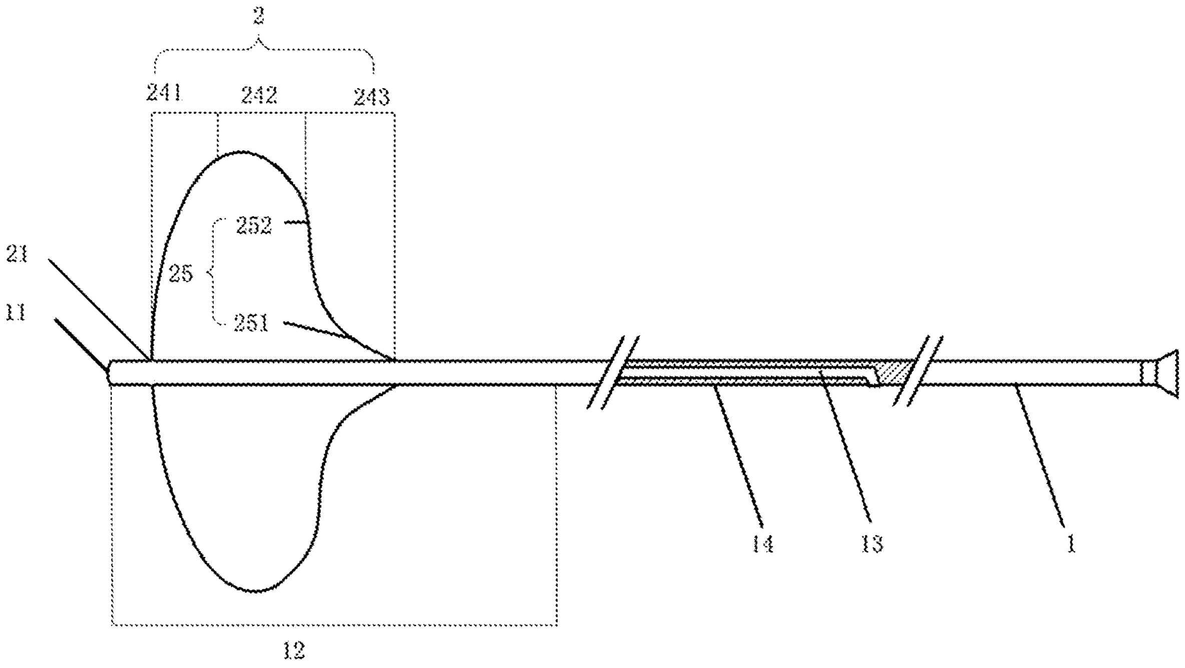
FIG. 14 shows a schematic view of the balloon device according to example 12.

FIG. 14 shows the structure of the balloon device when fully expanded in example 12, which was comprised of a balloon catheter 1 and a balloon 2. The balloon 2 was arranged at the front portion 12 of the balloon catheter. The diameter of the balloon catheter 1 was 1.8 F. The interior of the balloon catheter 1 was provided with a guide wire through hole 13 and a pressurized liquid channel 14. The pressurized liquid channel 14 was communicated with the interior of the balloon 2. The balloon 2 was comprised of a longitudinal front portion 241, a longitudinal middle portion 242 and a longitudinal rear portion 243.

Figure 15:
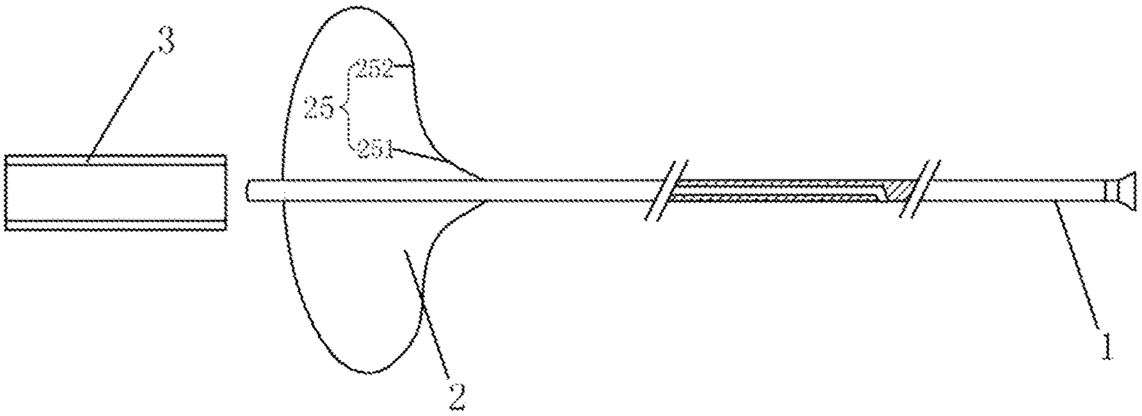
FIG. 15 shows a schematic view of the folding of the balloon device according to example 12.

As shown in FIG. 15, when folding the balloon 2, the sleeve 3 with an inner diameter of 5 mm was sleeved from the back side area of the concave arc shape 25, and the filling fluid (gas or liquid) inside the balloon 2 was evacuated at the same time, so that the area of the concave arc shape 25 could be embedded in the folded balloon 2, and most of the area of the concave arc shape 25 was folded inside. When fully expanded, the balloon 2 had a longitudinal dimension of 10 mm and a radial dimension of 15 mm, and its longitudinal section which was located at the longitudinal rear portion 243 had a concave arc shape 25. The concave arc shape 25 started from portion near the balloon catheter 251 and ended at the radial middle portion 252 of the balloon radially. The radial distance between the portion near the balloon catheter 251 and the centerline of the balloon catheter 1 was 2 mm, and the radial distance between the radial middle portion 252 and the centerline of the balloon catheter 1 was 3.75 mm [Here, the balloon 2 was fully expanded, and had a radial dimension of 15 mm, and radius of the balloon 2 was 7.5 mm].

The surface of the concave arc shape 25 was provided with a pharmaceutical composition 4, which comprised paclitaxel and iopromide. The pharmaceutical composition was formed into a pharmaceutical composition layer 4 with a thickness of about 50 microns. In the treatment, the guide wire was firstly set, wherein the guide wire was penetrated through the atrial septum of a heart. A fistula of appropriate size on the atrial septum of the heart was created. Then, the end coated balloon device was set at the fistula along with the guide wire. The front portion 12 of the balloon catheter was pushed to the far end and reached the target area through the fistula by PTCA (Percutaneous Transluminal Coronary Angioplasty) technology, then pressurized fluid was injected into the balloon 2 through the pressurized fluid channel 14. Under the hydraulic pressure, the balloon 2 was fully expanded, and the internal pressure in the balloon 2 was maintained. The surface of the front end portion 22 of the balloon 2 was in full contact with one side of the atrial septum at the fistula to be treated, and the pharmaceutical composition was quickly released to the contact area. After predetermined expansion time, the pressurized liquid was drawn out, and the balloon 2 was deflated and the balloon device was withdrawn to complete the treatment.

Example 13 [Combination of Example 11 and Example 12]

The balloon device disclosed in example 13 was a combination of the balloon device in example 11 and the balloon device in example 12, wherein the balloon device 1 adopts the balloon with concave arc shape 25 in the longitudinal rear portion 243 (i.e. the device disclosed in example 12), and the balloon device 2 adopts the balloon with concave arc shape 25 in the longitudinal front portion 241 (i.e. the device disclosed in example 11). A pharmaceutical composition layer 4 was provided on the surface of the area of the concave arc shape 25, and the pharmaceutical composition 4 comprised paclitaxel, rapamycin and iopamidol.

In the treatment, the front portion 12 of the balloon catheter of the balloon device 1 was pushed to the far end in the same way as that in example 12, and reaches the target area through the fistula, so that the surface of the concave arc shape 25 was fully in contact with one side of the atrial septum at the fistula to be treated. The balloon device 1 was withdrawn after the contact was completed. Then, in the same way as that in example 11, the front portion 12 of the balloon catheter of the balloon device 2 was pushed to the far end to reach the target area that does not pass through the fistula, make the surface of the concave arc shape 25 fully contact with the other side of the atrial septum at the fistula to be treated. The balloon device 2 was withdrawn after the contact was completed, so as to complete the treatment of the two sides of the atrial septum at the fistula in turn. It should be noted that during each treatment, the fistula itself can also be treated with pharmaceutical composition.

Example 14 [there is a Concave Area in the Middle of the Longitudinal Direction]

Figure 16:
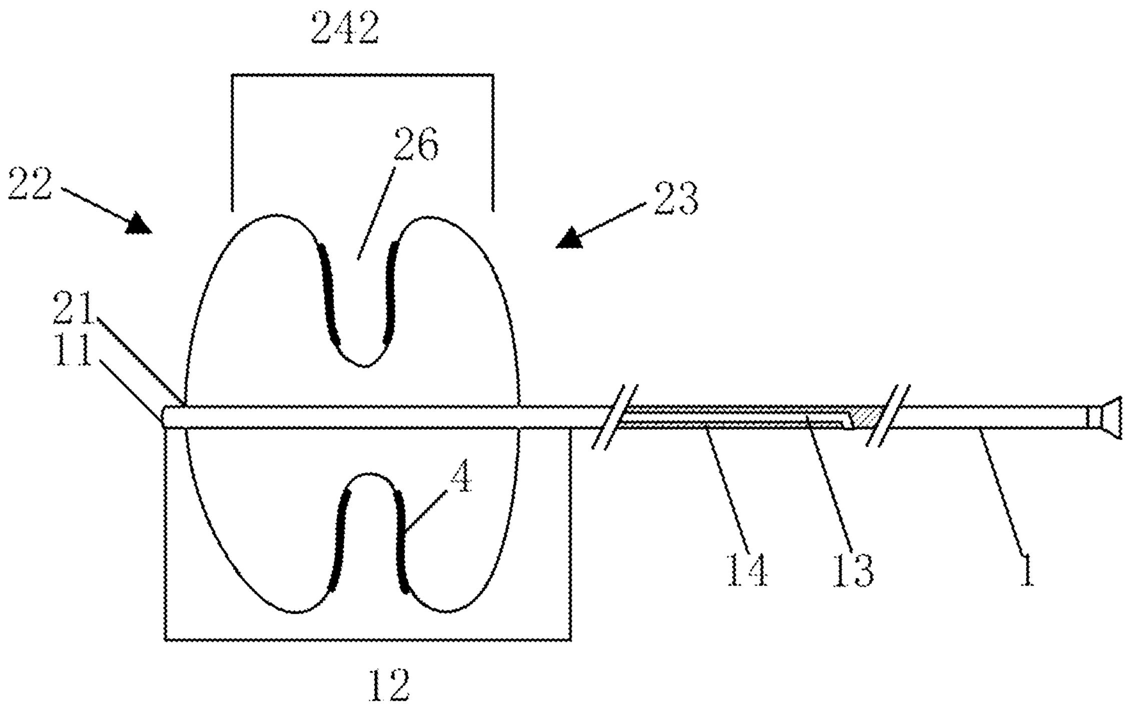
FIG. 16 shows a schematic view of the balloon device according to example 14.

FIG. 16 showed the structure of the balloon device when fully expanded in example 14, which was comprised of a balloon catheter 1 and a balloon 2. The balloon 2 was arranged at the front portion 12 of the balloon catheter. The diameter of the balloon catheter 1 was 2.0 F. The interior of the balloon catheter 1 was provided with a guide wire through hole 13 and a pressurized liquid channel 14. The pressurized liquid channel 14 was communicated with the interior of the balloon 2. The balloon 2 was comprised of a front end portion 22, a longitudinal middle portion 242 and a rear end portion 23.

The balloon 2 had a concave area 26 on its longitudinal section located in the longitudinal middle portion 242. The outer surface of the concave area 26 was provided with a pharmaceutical composition 4, which comprised paclitaxel, rapamycin, iopromide, and iopamidol. In the treatment, the front portion 12 of the balloon catheter was pushed to the far end target area by PTCA technology, so that the concave area 26 was located at the fistula, and then the pressurized fluid was injected into the balloon 2 through the pressurized fluid channel 14. Under the hydraulic pressure, the balloon 2 was fully expanded, and the internal pressure in the balloon 2 was maintained. The surface of the concave area 26 was in full contact with the fistula to be treated, and the drug was quickly released to the target area. After the predetermined expansion time, the pressurized liquid was drawn out, and the balloon 2 was deflated and the balloon device was withdrawn to complete the treatment.

In addition, the technical scheme disclosed in this application includes the following contents:

Embodiment 1. An end coated balloon device, comprising: a balloon catheter, and a balloon arranged on the balloon catheter, the balloon has a front end portion and a rear end portion in a longitudinal direction, and a pharmaceutical composition or pharmaceutical composition layer is provided on an outer surface of at least one of the front end portion and the rear end portion. The pharmaceutical composition layer has a thickness of about 1 micron to 100 microns, for example, 10 microns to 75 microns.

Embodiment 2. The balloon device according to embodiment 1, wherein the pharmaceutical composition is provided only on the outer surface of one of the front end portion and the rear end portion.

Embodiment 3. The balloon device according to embodiment 1, wherein the balloon catheter is provided with a guide wire through hole and a pressurized liquid channel, wherein the pressurized liquid channel is communicated with an interior of the balloon.

Embodiment 4. The balloon device according to embodiment 1, wherein the balloon is arranged at a front portion of the balloon catheter, and a distance between a front point of the balloon and a front point of the balloon catheter is about 5 to 20 mm.

Embodiment 5. The balloon device according to embodiment 1 or 2, wherein for the outer surface provided with the pharmaceutical composition, the pharmaceutical composition is only provided for a part with a radius greater than 2 mm, and the pharmaceutical composition is not provided on other outer surfaces of the balloon.

Embodiment 6. The balloon device according to embodiment 1, wherein a longitudinal section of the outer surface provided with the pharmaceutical composition has a concave arc shape, an circular arc shape, an elliptical arc shape, a parabola shape, a straight line shape, a broken line shape, an irregular curve shape, or a combination of two or more of them.

Embodiment 7. The balloon device according to embodiment 1, wherein the pharmaceutical composition comprises at least one of paclitaxel and rapamycin, and optionally, a drug carrier.

Embodiment 8. The balloon device according to any of embodiments 1-7, wherein a radial dimension of the balloon during expansion is 6 to 25 mm, such as 8 to 20 mm, such as 10 to 20 mm, such as 12 to 20 mm, such as 14 to 20 mm, such as 16 to 20 mm, such as 18 to 20 mm.

Embodiment 9. The balloon device according to any of embodiments 1-7, wherein the balloon is a non compliant balloon, a compliant balloon, or a semi compliant balloon.

Embodiment 10. A medical device, in particular for interventional treatment of percutaneous atrial septostomy, which comprises a balloon device according to any one of embodiments 1-9.

The above is only an exemplary example/embodiment of this application and is not used to limit the scope of protection of this application. The scope of protection of this application is determined by the claims.

The invention claimed is:

1. A balloon device, comprising:

a balloon catheter, and a balloon arranged on the balloon catheter, the balloon has a front end portion and a rear end portion in a longitudinal direction, and a pharmaceutical composition layer is provided only on an outer surface of at least one of the front end portion and the rear end portion, so that when contacting the balloon of the balloon device with an atrial septal fistula in front of the balloon, the pharmaceutical composition is delivered to the atrial septal fistula and the atrial septal fistula's periphery, wherein the balloon has a longitudinal dimension and a radial dimension, the longitudinal dimension is ⅔ or less of the radial dimension, the balloon device comprises only one balloon, the front end portion of the balloon is an end surface of the balloon which first reaches an area to be treated during operation and is an area from a front endpoint the balloon to, but not including, a radial farthest point of the balloon when expanded, the rear end portion of the balloon is a portion opposite to the front end portion and is an area from a rear endpoint of the balloon to, but not including, the radial farthest point of the balloon when expanded.

2. The balloon device according to claim 1, wherein the pharmaceutical composition layer is provided on the outer surface of only one of the front end portion and the rear end portion.

3. The balloon device according to claim 1, wherein the balloon catheter is provided with a guide wire through hole and a pressurized liquid channel, wherein the pressurized liquid channel is communicated with an interior of the balloon.

4. The balloon device according to claim 1, wherein the balloon is arranged at a front portion of the balloon catheter, and a distance between a front point of the balloon and a front point of the balloon catheter is 5 mm to 20 mm.

5. The balloon device according to claim 1, wherein for the outer surface provided with the pharmaceutical composition layer, the pharmaceutical composition layer is only provided on a part of the balloon having a radius greater than 2 mm, and the pharmaceutical composition layer is not provided on other outer surfaces of the balloon.

6. The balloon device according to claim 1, wherein a longitudinal section of the outer surface provided with the pharmaceutical composition layer has a concave arc shape, a circular arc shape, an elliptical arc shape, a parabola shape, a straight line shape, a broken line shape, or a combination of two or more of these shapes.

7. The balloon device according to claim 1, wherein the pharmaceutical composition comprises at least one of paclitaxel and rapamycin, and a drug carrier.

8. The balloon device according to claim 1, wherein the longitudinal dimension of the balloon is 5 mm to 16 mm, and the radial dimension of the balloon during expansion is 10 mm to 25 mm.

9. The balloon device according to claim 1, wherein the longitudinal dimension is ½ or less of the radial dimension, and the radial dimension of the balloon during expansion is 15 mm to 20 mm.

10. A method for treating an atrial septal fistula by using a medical device comprising a balloon device according to claim 1, wherein the method comprises:

contacting the balloon of the balloon device with the atrial septal fistula and the atrial septal fistula's periphery.

* * * * *